(12) United States Patent
Zou et al.

(10) Patent No.: US 11,331,339 B2
(45) Date of Patent: May 17, 2022

(54) COMPOUND COMPOSITION WITH FUNCTION OF PROMOTING BONE AND JOINT HEALTH AND APPLICATION THEREOF

(71) Applicant: Chenland Nutritionals, Inc., Pomona, CA (US)

(72) Inventors: Shengcan Zou, Qingdao (CN); Li Li, Qingdao (CN); Lei Zong, Qingdao (CN); Jiancheng Zong, Qingdao (CN); Shanglong Wang, Qingdao (CN); Zengliang Zhang, Qingdao (CN)

(*) Notice: Subject to any disclaimer, the term of this patent is extended or adjusted under 35 U.S.C. 154(b) by 108 days.

(21) Appl. No.: 16/846,455

(22) Filed: Apr. 13, 2020

(65) Prior Publication Data

US 2020/0237805 A1 Jul. 30, 2020

Related U.S. Application Data

(63) Continuation of application No. PCT/CN2019/111794, filed on Oct. 18, 2019.

(30) Foreign Application Priority Data

Sep. 30, 2019 (CN) .......................... 201910943736.5

(51) Int. Cl.
| | |
|---|---|
| *A61K 31/737* | (2006.01) |
| *A61K 47/42* | (2017.01) |
| *A61K 31/7008* | (2006.01) |
| *A61K 36/296* | (2006.01) |
| *A61P 19/02* | (2006.01) |
| *A61K 36/8945* | (2006.01) |
| *A61K 36/126* | (2006.01) |
| *A61K 36/39* | (2006.01) |
| *A61K 36/537* | (2006.01) |
| *A61K 9/00* | (2006.01) |

(52) U.S. Cl.
CPC .......... *A61K 31/737* (2013.01); *A61K 9/0056* (2013.01); *A61K 31/7008* (2013.01); *A61K 36/126* (2013.01); *A61K 36/296* (2013.01); *A61K 36/39* (2013.01); *A61K 36/537* (2013.01); *A61K 36/8945* (2013.01); *A61K 47/42* (2013.01); *A61P 19/02* (2018.01)

(58) Field of Classification Search
None
See application file for complete search history.

(56) References Cited

U.S. PATENT DOCUMENTS

2017/0095539 A1* 4/2017 Tan .................. A61K 31/10

FOREIGN PATENT DOCUMENTS

CN 110664902 A * 1/2020

OTHER PUBLICATIONS

CN110664902A, Espacenet machine translation.*
Ou-yang, S.-H., et al., Dioscorea nipponica Makino: a systematic review on its ethnobotany, phytochemical and pharmacological profiles, Chem Cent J. 2018; 12: 57.*

* cited by examiner

*Primary Examiner* — H. Sarah Park

(57) ABSTRACT

The present invention discloses a compound composition with function of promoting bone and joint health and an application thereof. In the present invention, glucosamine is combined with collagen, chondroitin sulfate and traditional Chinese medicine extract to prepare the compound composition with function of promoting bone and joint health. The compound composition can shorten onset time. At the same time, the traditional Chinese medicine extract for treating the bone and joint problems is added, to reduce the market impact of adding only modern joint health ingredients. Moreover, the compound composition disclosed by the present invention can be used as a dietary supplement or health food raw material for preventing or treating moderate to mild osteoarthritis. Thus, the compound composition disclosed by the present invention is suitable for promotion and application.

3 Claims, 1 Drawing Sheet

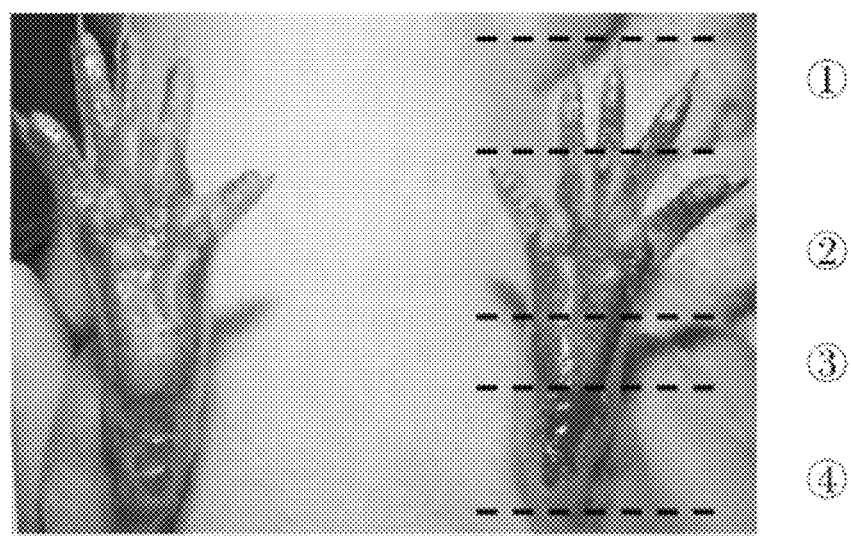

COMPOUND COMPOSITION WITH FUNCTION OF PROMOTING BONE AND JOINT HEALTH AND APPLICATION THEREOF

TECHNICAL FIELD

The present invention belongs to the technical field of natural medicine, and particularly relates to a compound composition with function of promoting bone and joint health and an application thereof.

BACKGROUND

With the trend of worldwide aging population, osteoarthritic patients are constantly increased. Although glucosamine is widely used as a dietary supplement for the prevention and adjuvant treatment of osteoarthritis, the main components of the glucosamine are very slow in preventing arthritis, and are used in large quantities in some cases, thereby requiring the patients to take several large doses of pills each day. Although the scientific principle of preventing the arthritis using the glucosamine is convincing, it is not as compelling as the components in other industries, such as Omega-3s, so that the current research progress on the efficacy and the principle of the glucosamine still has some problems.

At present, many pharmaceutical ingredients for alleviating the arthritis appear on the market, such as chondroitin sulfate, dimethyl sulfone, hyaluronic acid, collagen and curcumin. Commercially available drugs for the prevention and adjuvant treatment of the arthritis are formed by combining the glucosamine with one or more of the above pharmaceutical ingredients. The above pharmaceutical combination is only physical superposition of various pharmaceutical ingredients. Although the effect is slightly better than that of the glucosamine, the problems of slow effect, large daily dosage and high cost still exist.

Therefore, how to develop a compound composition with function of promoting bone and joint health having rapid effect, small daily dosage and low cost is a problem to be urgently solved by those skilled in the art.

SUMMARY

In view of this, the purpose of the present invention is to provide a compound composition with function of promoting bone and joint health and an application of the compound composition in preparation of health food with respect to the problems in the prior art.

To achieve the above purpose, the present invention adopts the following technical solution:

A compound composition with function of promoting bone and joint health is provided. The compound composition is composed of the following raw materials in parts by weight:

| | |
|---|---|
| glucosamine | 1.0-3.0 parts; |
| collagen | 0.1-1.0 part; |
| chondroitin sulfate | 0.1-1.0 part; |
| traditional Chinese medicine extract | 0.1-1.0 part. |

The compound composition with function of promoting bone and joint health disclosed by the present invention combines the glucosamine with the collagen, the chondroitin sulfate and the traditional Chinese medicine extract, and adds traditional Chinese medicine plant extracts based on the glucosamine, the chondroitin sulfate and the collagen as the material basis. From the results of pharmacodynamic tests, in a certain period of administration, the compound composition with the traditional Chinese medicine plant extracts has better effect than the composition without the traditional Chinese medicine plant extracts, which indirectly proves that in a certain period of time, the addition of the traditional Chinese medicine plant extracts can play a role in alleviating joint discomfort more rapidly and obviously, thereby achieving the purpose of shortening the onset time. Moreover, the compound composition has small daily dosage and low cost, and is suitable for promotion and application.

Preferably, the compound composition is composed of the following raw materials in parts by weight:

| | |
|---|---|
| glucosamine | 1.0-1.5 parts; |
| collagen | 0.2-0.7 part; |
| chondroitin sulfate | 0.1-0.3 part; |
| traditional Chinese medicine extract | 0.1-0.5 part. |

The compound composition is composed of the following raw materials in parts by weight:

| | |
|---|---|
| glucosamine | 1.2 parts; |
| collagen | 0.4 part; |
| chondroitin sulfate | 0.2 part; |
| traditional Chinese medicine extract | 0.35 part. |

It should be noted that the amount of the traditional Chinese medicine extract added to the compound composition disclosed by the present invention is reasonable, which is between 2 and 5 flavors. The types of the traditional Chinese medicine are screened through scientific guidance such as network pharmacology and traditional Chinese medicine theory to determine the main active substances. Animal pharmacodynamic tests are used for verification, so that the compound composition with function of promoting bone and joint health achieves the purposes of fast effect, obvious action, small daily dosage and low cost.

Preferably, the traditional Chinese medicine extract is prepared by extracting traditional Chinese medicine, and the traditional Chinese medicine extract is a mixture composed of at least two extracts of an epimedium brevicornu extract, a salviae miltiorrhizae extract, a dioscorea nipponica makino extract, a rhizoma drynariae extract and a dodder extract.

The traditional Chinese medicine comprises the following components in parts by weight: 7-12 parts of epimedium brevicornu, 0.5-3 parts of salviae miltiorrhizae, 6.5-9 parts of dioscorea nipponica makino, 1-5 parts of rhizoma drynariae and 1-5 parts of dodder.

It is worth mentioning that the traditional Chinese medicine used in the traditional Chinese medicine extract disclosed by the present invention is screened through scientific basis (from prescriptions related to bone health), organically combined, and compounded according to the traditional Chinese medicine theory rather than being simply superposed according to single traditional Chinese medicine effect. The specific effects of all kinds of traditional Chinese medicine are as follows:

Dioscorea nipponica makino: [actions and indications] dispelling wind and eliminating dampness, relaxing muscles and tendons, regulating the meridians, promoting blood circulation to arrest pain and relieving cough and asthma. It is used for rheumatism, joint swelling, pain numbness, flutter injury, sudden sprain in the lumbar region, cough and asthma.

Epimedium brevicornu: [actions and indications] replenishing kidney yang, strengthening the bones and muscles and eliminating wind and dampness. It is used for kidney-Yang deficiency, impotence and seminal emission, flaccidity of muscles and bones, arthralgia due to wind-dampness, and numbness and muscular constriction.

Salviae miltiorrhizae: [actions and indications] promoting blood circulation to remove blood stasis, inducing menstruation to relieve menalgia, clearing away heart fire to relieve restlessness, and cooling blood to treat boils. It is used for chest stuffiness and pains, abdominal pain, concretions and gatherings, pyretic arthralgia pain, dysphoria and agrypnia, irregular menstruation, dysmenorrhea and amenorrhoea, and sore pain.

Rhizoma drynariae: [actions and indications] healing and acesodyne, replenishing kidney and strengthening the bone, and eliminating wind and removing beverage for external use. It is used for flutter, sprain and contusion, fracture of muscles and bones, lumbago due to kidney-asthenia, flaccidity of muscles and bones, hiccough and deaf, gomphiasis, and alopecia areata and vitiligo for external use.

Dodder: [actions and indications] tonifying the liver and kidney, securing essence and reducing urination, preventing miscarriage, improving eyesight, relieving diarrhea, and eliminating wind and removing beverage for external use. It is used for deficiency of liver and kidney, soreness and weakness of waist and knees, impotence and seminal emission, enuresis and frequent micturition, vaginal bleeding due to deficiency of the kidney during pregnancy, fetal irritability, dizziness and tinnitus, spleen and kidney deficiency, and external treatment of vitiligo.

Through the analysis of the effects of various flavors of traditional Chinese herbal medicine, dioscorea nipponica makino and epimedium brevicornu have the action of eliminating wind and dampness, but have own focuses. The dioscorea nipponica makino focuses on relaxing muscles and tendons, regulating the meridians and promoting blood circulation to arrest pain; and the epimedium brevicornu focuses on replenishing kidney yang and strengthening the bones and muscles. The effects of promoting blood circulation to arrest pain, relaxing muscles and tendons and strengthening the bone can be achieved only by jointly using the dioscorea nipponica makino and the epimedium brevicornu. Therefore, the effects of the dioscorea nipponica makino and the epimedium brevicornu are not simply superposed, but are compounded with each other. For this, the prior art does not give the technical inspiration of using one of the dioscorea nipponica makino and the epimedium brevicornu and deleting the dioscorea nipponica makino from the prescription.

In addition, in the prescription of the traditional Chinese medicine, the salviae miltiorrhizae has the effect of activating blood circulation to dissipate blood stasis, and the rhizoma drynariae has the effects of replenishing kidney and strengthening the bone. The above traditional Chinese medicines are compounded according to the traditional Chinese medicine theory to prepare the compound composition having quick effects, obvious curative effects and function of promoting bone and joint health.

In addition, in the prior art, although the usual dosage of each flavor of traditional Chinese medicine is known, the prescription is an organic whole after multiple flavors of medicine are compounded with respect to the diseases, and the pharmaceutical effect is not the same as that of the simple superposition of each flavor of traditional Chinese medicine based on the usual dosage. The amount of each flavor of traditional Chinese medicine in the prescription cannot be determined according to the usual dosage of the medicine. The dosage ratio of the medicine is determined by various considerations such as characteristics of the medicine and the compatibility of the adjuvants, and is not simply selected through experimental means such as comparison method and orthogonal method.

Another purpose of the present invention is to provide an application of the compound composition with function of promoting bone and joint health in preparation of health food.

The compound composition disclosed by the present invention can be used as a dietary supplement or health food raw material for preventing or treating moderate to mild osteoarthritis.

It can be known from the above technical solution that compared with the prior art, the present invention provides a compound composition with function of promoting bone and joint health and an application thereof, and has the following excellent effects:

In one aspect, the compound composition disclosed by the present invention has obvious advantages in onset time, anti-inflammation and pain alleviation compared with single glucosamine and the combination of the glucosamine, the collagen and the chondroitin; and in another aspect, the selected traditional Chinese medicine is screened from prescriptions related to bone health, organically combined, and compounded according to the traditional Chinese medicine theory so that the compound composition has the advantages of rapid effect and small daily dosage.

Therefore, in conclusion, with respect to the general problems of large dosage, high cost, slow effect, easy impact caused by new products and inadaptation to market needs in the existing commercially available products, in the present invention, the glucosamine is combined with the collagen, the chondroitin sulfate and the traditional Chinese medicine extract to prepare the compound composition with function of promoting bone and joint health. The compound composition can shorten onset time. At the same time, the traditional Chinese medicine extract for treating the bone and joint problems is added, to reduce the market impact of adding only modern joint health ingredients. The compound composition disclosed by the present invention is suitable for promotion and application.

BRIEF DESCRIPTION OF THE DRAWINGS

To more clearly describe the technical solution in the embodiments of the present invention or in the prior art, the drawings required to be used in the description of the embodiments or the prior art will be simply presented below. Apparently, the drawings in the following description are merely the embodiments of the present invention, and for those ordinary skilled in the art, other drawings can also be obtained according to the provided drawings without contributing creative labor.

FIG. 1 is a diagram of a pain scoring standard of the present invention.

DETAILED DESCRIPTION

The technical solution disclosed by the present invention will be clearly and fully described below in combination with the embodiments of the present invention. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

Embodiments of the present invention disclose a compound composition having rapid effect, small daily dosage and low cost. The compound composition has the function of promoting bone and joint health, and can be used as a dietary supplement or health food raw material for preventing or treating moderate to mild osteoarthritis.

To better understand the present invention, the present invention is further described in detail below by the following embodiments, but shall not be interpreted as a limitation to the present invention. Some non-essential improvements and adjustments made by those skilled in the art according to the contents of the present invention shall also be deemed to fall within the protection scope of the present invention.

The present invention discloses a compound composition with function of promoting bone and joint health. The compound composition is composed of the following raw materials in parts by weight:

| | |
|---|---|
| glucosamine | 1.0-3.0 parts; |
| collagen | 0.1-1.0 part; |
| chondroitin sulfate | 0.1-1.0 part; |
| traditional Chinese medicine extract | 0.1-1.0 part. |

To further optimize the above technical solution, the traditional Chinese medicine extract is prepared by extracting traditional Chinese medicine, and the traditional Chinese medicine extract is a mixture composed of at least two extracts of an epimedium brevicornu extract, a salviae miltiorrhizae extract, a dioscorea nipponica makino extract, a rhizoma drynariae extract and a dodder extract.

To further optimize the above technical solution, the traditional Chinese medicine comprises the following components in parts by weight: 7-12 parts of epimedium brevicornu, 0.5-3 parts of salviae miltiorrhizae, 6.5-9 parts of dioscorea nipponica makino, 1-5 parts of rhizoma drynariae and 1-5 parts of dodder.

The present invention also discloses an application of the compound composition with function of promoting bone and joint health in preparation of health food.

The technical solution disclosed by the present invention is further described below in combination with specific embodiments.

Embodiment 1

A compound composition with function of promoting bone and joint health is provided. The compound composition is composed of the following raw materials in parts by weight:

| | |
|---|---|
| glucosamine | 1.2 parts; |
| collagen | 0.9 part; |
| chondroitin sulfate | 0.8 part; |
| traditional Chinese medicine extract | 0.2 part. |

Embodiment 2

A compound composition with function of promoting bone and joint health is provided. The compound composition is composed of the following raw materials in parts by weight:

| | |
|---|---|
| glucosamine | 2.8 parts; |
| collagen | 0.2 part; |
| chondroitin sulfate | 0.5 part; |
| traditional Chinese medicine extract | 0.5 part. |

Embodiment 3

A compound composition with function of promoting bone and joint health is provided. The compound composition is composed of the following raw materials in parts by weight:

| | |
|---|---|
| glucosamine | 1.5 parts; |
| collagen | 0.7 part; |
| chondroitin sulfate | 0.3 part; |
| traditional Chinese medicine extract | 0.6 part. |

Embodiment 4

A compound composition with function of promoting bone and joint health is provided. The compound composition is composed of the following raw materials in parts by weight:

| | |
|---|---|
| glucosamine | 2.5 parts; |
| collagen | 0.5 part; |
| chondroitin sulfate | 0.3 part; |
| traditional Chinese medicine extract | 0.35 part. |

Embodiment 5

A compound composition with function of promoting bone and joint health is provided. The compound composition is composed of the following raw materials in parts by weight:

| | |
|---|---|
| glucosamine | 1.2 parts; |
| collagen | 0.4 part; |
| chondroitin sulfate | 0.2 part; |
| traditional Chinese medicine extract | 0.35 part. |

Embodiment 6

The traditional Chinese medicine used by the traditional Chinese medicine extract in the compound composition with function of promoting bone and joint health disclosed by any of the above embodiments 1-5 comprises the following components in parts by weight:

8 parts of epimedium brevicornu, 3 parts of salviae miltiorrhizae, 9 parts of dioscorea nipponica makino, 2 parts of rhizoma drynariae and 4 parts of dodder.

The preparation method of the traditional Chinese medicine extract is as follows:

extracting each flavor of medicine with an alcohol extraction technology, purifying with macroporous resin; concentrating and spray-drying to finally obtain the traditional Chinese medicine extracts.

Embodiment 7

The traditional Chinese medicine used by the traditional Chinese medicine extract in the compound composition with function of promoting bone and joint health disclosed by any of the above embodiments 1-5 comprises the following components in parts by weight:

10 parts of epimedium brevicornu, 2 parts of salviae miltiorrhizae, 8 parts of dioscorea nipponica makino, 4 parts of rhizoma drynariae and 2 parts of dodder.

The preparation method of the traditional Chinese medicine extract is as follows:

extracting each flavor of medicine with an alcohol extraction technology; purifying with macroporous resin; concentrating and spray-drying to finally obtain the traditional Chinese medicine extracts.

Embodiment 8

The traditional Chinese medicine used by the traditional Chinese medicine extract in the compound composition with function of promoting bone and joint health disclosed by any of the above embodiments 1-5 comprises the following components in parts by weight:

12 parts of epimedium brevicornu, 0.8 part of salviae miltiorrhizae, 7.2 parts of dioscorea nipponica makino, 3 parts of rhizoma drynariae and 3 parts of dodder.

The preparation method of the traditional Chinese medicine extract is as follows:

extracting each flavor of medicine with an alcohol extraction technology; purifying with macroporous resin; concentrating and spray-drying to finally obtain the traditional Chinese medicine extracts.

Specifically, the preparation method of the above compound composition with function of promoting bone and joint health comprises the following steps:

(1) extracting each flavor of medicine with an alcohol extraction technology; purifying with macroporous resin; concentrating and spray-drying to obtain the traditional Chinese medicine extracts;

(2) uniformly mixing the traditional Chinese medicine extracts obtained in the above preparation with the glucosamine, the collagen and the chondroitin sulfate to obtain the compound composition.

Exemplarily, as seen below, embodiment 9 to embodiment 11 disclose a preparation method of the compound composition with function of promoting bone and joint health.

Embodiment 9

A compound composition with function of promoting bone and joint health is composed of the following raw materials in parts by weight: 100 g of glucosamine, 30 g of collagen, 10 g of chondroitin sulfate and traditional Chinese medicine extract which is obtained by extracting 700 g of epimedium brevicornu medicine, 100 g of salviae miltiorrhizae medicine and 700 g of dioscorea nipponica makino medicine.

The preparation method of the compound composition comprises the following specific steps:

(1) adding 8 times the amount of 70% ethanol to the epimedium brevicornu medicine; conducting heating reflux extraction twice for 1.5 h each time; merging the extracting solutions; purifying; concentrating; adding 10% β-cyclodextrin; spray-drying at 200° C.; and filtering with a 80-mesh sieve to obtain an epimedium brevicornu extract;

(2) adding 8 times the amount of 80% ethanol to the salviae miltiorrhizae medicine; conducting heating reflux extraction twice for 1.5 h each time; merging the extracting solutions; purifying; concentrating; adding 10% β-cyclodextrin; spray-drying at 200'C; and filtering with a 80-mesh sieve to obtain a salviae miltiorrhizae extract;

(3) adding 8 times the amount of 70% ethanol to the dioscorea nipponica makino medicine; conducting heating reflux extraction three times for 1.5 h each time; merging the extracting solutions; purifying; concentrating; adding 10% β-cyclodextrin; spray-drying at 200'C; and filtering with a 80-mesh sieve to obtain a dioscorea nipponica makino extract;

(4) mixing the traditional Chinese medicine extracts obtained in the above preparation, and uniformly mixing with the glucosamine, the collagen and the chondroitin sulfate to obtain the compound composition of 100 times prescribed daily dosage.

Embodiment 10

A compound composition with function of promoting bone and joint health is composed of the following raw materials in parts by weight: 240 g of glucosamine, 40 g of collagen, 60 g of chondroitin sulfate and traditional Chinese medicine extract which is obtained by extracting 2000 g of epimedium brevicornu medicine, 600 g of rhizoma drynariae medicine and 600 g of dodder medicine.

The preparation method of the compound composition comprises the following specific steps:

(1) adding 10 times the amount of 70% ethanol to the epimedium brevicornu medicine; conducting heating reflux extraction twice for 2 h each time; merging the extracting solutions; purifying; concentrating; adding 15% β-cyclodextrin; spray-drying at 200° C.; and filtering with a 80-mesh sieve to obtain an epimedium brevicornu extract;

(2) adding 20 times the amount of 80% ethanol to the rhizoma drynariae medicine; conducting heating reflux extraction twice for 1.5 h each time; merging the extracting solutions; purifying; concentrating; adding 10% β-cyclodextrin; spray-drying at 200° C.; and filtering with a 80-mesh sieve to obtain a rhizoma drynariae extract;

(3) adding 6 times the amount of 75% ethanol to the dodder medicine; conducting heating reflux extraction twice for 2 h each time; merging the extracting solutions; purifying; concentrating; adding 10% β-cyclodextrin; spray-drying at 200° C.; and filtering with a 80-mesh sieve to obtain a dodder extract;

(4) mixing the traditional Chinese medicine extracts obtained in the above preparation, and uniformly mixing with the glucosamine, the collagen and the chondroitin sulfate to obtain the compound composition of 200 times prescribed daily dosage.

Embodiment 11

A compound composition with function of promoting bone and joint health is composed of the following raw materials in parts by weight: 150 g of glucosamine, 50 g of collagen, 60 g of chondroitin sulfate and traditional Chinese medicine extract which is obtained by extracting 2000 g of epimedium brevicornu medicine and 100 g of salviae miltiorrhizae medicine.

The preparation method of the compound composition comprises the following specific steps:

(1) adding 10 times the amount of 70% ethanol to the epimedium brevicornu medicine; conducting heating reflux extraction twice for 2 h each time; merging the extracting solutions; purifying; concentrating; adding 15% β-cyclodextrin; spray-drying at 200° C.; and filtering with a 80-mesh sieve to obtain an epimedium brevicornu extract;

(2) adding 10 times the amount of 80% ethanol to the salviae miltiorrhizae medicine; conducting heating reflux extraction twice for 2 h each time; merging the extracting solutions; purifying; concentrating; adding 10% β-cyclodextrin; spray-drying at 200'C; and filtering with a 80-mesh sieve to obtain a salviae miltiorrhizae extract;

(3) mixing the traditional Chinese medicine extracts obtained in the above preparation, and uniformly mixing with the glucosamine, the collagen and the chondroitin sulfate to obtain the compound composition of 100 times prescribed daily dosage.

Each embodiment in the description is described in a progressive way. The difference of each embodiment from each other is the focus of explanation. The same and similar parts among all of the embodiments can be referred to each other.

The contents of the present invention are not limited to the contents of the above embodiments, and a combination of one or more embodiments can also achieve the purposes of the present invention.

In order to further verify the excellent effects of the present invention, the inventors also conduct the following experiment.

Test I:

Function of the compound composition with function of promoting bone and joint health in anti-inflammation.

Male wistar rats are randomly divided into a control group, a model group and an experimental group. Each group includes 10 rats. The rats are injected with papain for molding. The rats are administered for 28 days at the same time of molding. Before the rats are put to death, blood is taken from the abdominal vein and centrifuged to obtain serum. The IL-1β content is detected. Specific results are shown in Table 1:

TABLE 1

Levels of Inflammatory Factor IL-1β in Serums of Rats in Each Group

| Groups | Number of animals (piece) | Daily dosage mg/kg | IL-1β content (ng/L) |
|---|---|---|---|
| Blank group | 12 | Equal-volume normal saline | 5.063 ± 0.721 |
| Model group | 12 | Equal-volume normal saline | 8.08 ± 1.176 |
| Experimental administration group | 12 | 169.2 | 6.573 ± 0.6719* |
| Glucosamine sulfate control group 1 | 12 | 126 | 9.456 ± 1.657 |
| Glucosamine + chondroitin sulfate + collagen control group 2 | 12 | 207 | 8.975 ± 0.7605 |

The blank group includes normal rats for arthritis modeling. The model group includes rats not administered after modeling. The experimental administration group administers the product of the present invention to the rats. The glucosamine sulfate control group administers glucosamine to the rats. The glucosamine+chondroitin sulfate+collagen control group administers glucosamine+chondroitin sulfate+collagen to the rats. IL-1β is an inflammatory factor in the serum. Normal rats contain the lowest levels of inflammatory factors, and the rats with arthritis but not administered contain the highest levels of inflammatory factors. If different products are administered to rats, the degree of arthritis is alleviated to a certain extent and the levels of inflammatory factors in the rats are reduced to be lower than that of the highest model group, but higher than normal rats. It can be seen from the data in Table 1 that the level of the inflammatory factor of the experimental administration group, i.e., the product group of the present invention, is obviously different from that of the model group, and is lower than those of the control group 1 and the control group 2, which proves that the product has the function of anti-inflammation and has better effect than the single glucosamine and the combination of the glucosamine and the pharmaceutical ingredients.

In addition, to verify the technical solution of the present invention and small daily dosage of the single glucosamine, the inventor respectively experiments the male wistar rats in the same administration time and under the same administration dosage, and detects the IL-6 content in the serum. Specific results are shown in Table 2:

TABLE 2

Levels of Inflammatory Factor IL-6 in Serums of Rats in Each Group

| Groups | Number of animals (piece) | Daily dosage mg/kg | IL-6 content (ng/L) |
|---|---|---|---|
| Blank group | 10 | Equal-volume normal saline | 102.03 ± 6.78 |
| Model group | 10 | Equal-volume normal saline | 158.79 ± 17.53 |
| Experimental administration group | 10 | 125 | 142.59 ± 17.17 * |
| Glucosamine sulfate control group | 10 | 125 | 146.19 ± 18.15 |

It can be seen from the data in Table 2 that in the same administration time and under the same administration dosage, in reducing the inflammatory factor IL-6, the experiment administration group is obviously lower than the model group. The glucosamine sulfate control group is not obviously lower than the model group. The inflammatory factor content in the serum in the experimental administration group is lower than that in the glucosamine sulfate group, which indicates that the formula product has advantages over the single glucosamine in terms of anti-inflammation, proving that the same effect can be achieved with less dosage.

Test II:

Function of the compound composition with function of promoting bone and joint health in pain alleviation.

Male wistar rats are randomly divided into a control group, a model group and an experimental group. Each group includes 10 rats. The rats are injected with papain for molding. The rats are administered for 28 days at the same time of molding. Before the rats are put to death, the tenderness thresholds at modeling joints are measured with a tenderness meter. Specific results are shown in Table 3:

TABLE 3

Results of Tenderness Thresholds of Rats in Each Group

| Groups | Number of animals (piece) | Daily dosage mg/kg | Tenderness thresholds (newton) |
| --- | --- | --- | --- |
| Blank group | 12 | Equal-volume normal saline | 6.348 ± 0.2191 |
| Model group | 12 | Equal-volume normal saline | 5.681 ± 0.2264 |
| Experimental administration group | 12 | 169.2 | 6.212 ± 0.1607 |
| Glucosamine sulfate control group 1 | 12 | 126 | 5.607 ± 0.2602 |
| Glucosamine + chondroitin sulfate + collagen control group 2 | 12 | 207 | 5.922 ± 0.1346 |

Normal rats in the blank group do not suffer from arthritis, and their joints can withstand larger forces when pressed. The rats in the model group do not receive treatment of arthritis, are sensitive to pain, and withstand smaller forces when pressed. The rats administered with the product can alleviate the arthritis to a certain extent, and withstand larger forces than the model group when pressed. It can be seen from the data in Table 3 that the experimental administration group withstand larger forces than the model group, proving the function of alleviating arthritis pain, and also withstand larger forces than the control group 1 and the control group 2, proving that the product has the function of alleviating the tenderness and has better effect than the single glucosamine and the combination of the glucosamine and the pharmaceutical ingredients.

In addition, the applicant tests the influences of different traditional Chinese medicine combinations on the tenderness thresholds of the rats. Specific results and analysis are shown in test III.

Test III:

Male wistar rats are randomly divided into a model group, an experimental administration group 1, an experimental administration group 2 and an experimental administration group 3. Each group includes 10 rats. The rats are injected with papain for molding. The rats are administered for 28 days at the same time of molding. Before the rats are put to death, the tenderness thresholds at modeling joints are measured with a tenderness meter. Specific results are shown in Table 4: In the experimental administration group 1, the rats are administered with the product of the present invention prepared by the combination of three kinds of traditional Chinese medicine of epimedium brevicornu, salviae miltiorrhizae and dioscorea nipponica makino. In the experimental administration group 2, the rats are administered with the product of the present invention prepared by the combination of two kinds of traditional Chinese medicine of dodder and rhizoma drynariae. In the experimental administration group 3, the rats are administered with the product of the present invention prepared by the combination of five kinds of traditional Chinese medicine of epimedium brevicornu, salviae miltiorrhizae, dioscorea nipponica makino, dodder and rhizoma drynariae.

TABLE 4

Influences of Different Traditional Chinese Medicine Combinations on Tenderness Thresholds of Rats

| Groups | Number of animals (piece) | Daily dosage mg/kg | Tenderness thresholds (kPa) |
| --- | --- | --- | --- |
| Blank group | 10 | Equal-volume normal saline | 450.03 ± 6.78 |
| Model group | 10 | Equal-volume normal saline | 208.79 ± 17.53 |
| Experimental administration group 1 | 10 | 55 | 292.59 ± 17.17 ** |
| Experimental administration group 2 | 10 | 50 | 264.19 ± 18.15* |
| Experimental administration group 3 | 10 | 75 | 281.64 ± 16.44* |

Normal rats in the blank group do not suffer from arthritis, and their joints can withstand larger forces when pressed. The rats in the model group do not receive treatment of arthritis, are sensitive to pain, and withstand smaller forces when pressed. The rats administered with the product can alleviate the arthritis to a certain extent, and withstand larger forces than the model group when pressed. It can be seen from the data in Table 4 that the experimental administration group withstand larger forces than the model group, proving the function of alleviating arthritis pain. Meanwhile, the tenderness threshold of the experimental administration group 1 is larger than those of the experimental administration group 2 and the experimental administration group 3, thereby proving that addition of formula traditional Chinese medicine in the product has the function of alleviating the arthritis pain and different traditional Chinese medicine combinations have different effects.

Test IV:

Function of the compound composition with function of promoting bone and joint health in pain alleviation.

Male wistar rats are randomly divided into a control group, a model group and an experimental group. Each group includes 10 rats. The rats are injected with papain for molding. The rats are administered for 28 days at the same time of molding. Before the rats are put to death, the left and right soles of the rats are evenly imprinted with printing ink of the same color and the rats walk by 0.4 m on a self-made semi-closed rat walking passage. The sole marks are photographed. Three persons independently score the walking pain based on the sole photos according to the following scoring standard for walking pain and measure the walking pain (when the limbs have a pain reaction, the rats move with the minimum contact area of the paws to reduce the pressure on the affected limbs; and when the left and right feet are uneven in stress and the gait is changed, the colors of the soles are different).

The scoring standard for the pain is shown in FIG. 1. The sole is divided into four regions: if one region of the left sole is darker than the right sole, the score is 1; if two regions are darker, the score is 2; and the score is added in sequence (0-4 scores).

Specific results are shown in Table 5:

TABLE 5

Results of Walking Pain of Rats in Each Group

| Groups | Number of animals (piece) | Daily dosage mg/kg | Scores of walking pain |
|---|---|---|---|
| Blank group | 12 | Equal-volume normal saline | 0.08333 ± 0.08333 |
| Model group | 12 | Equal-volume normal saline | 0.6364 ± 0.1521 |
| Experimental administration group | 12 | 169.2 | 0.45 ± 0.25 |
| Glucosamine sulfate control group 1 | 12 | 126 | 0.5 ± 0.2303 |
| Glucosamine + chondroitin sulfate + collagen control group 2 | 12 | 207 | 0.5833 ± 0.2876 |

Normal rats in the blank group do not suffer from arthritis, and their feet can normally touch the ground with force when walking. The rats in the model group do not receive treatment of arthritis, are sensitive to pain, and do not dare to force the feet when walking. The rats administered with the product can alleviate the arthritis to a certain extent, and can walk slightly normally, so as to reflect the degree of arthritis according to the walking scores. It can be seen from the data in Table 5 that the pain score of the experimental administration group is less than that of the model group, proving the function of alleviating arthritis pain, and also less than those of the control group 1 and the control group 2, proving that the product has the function of alleviating the walking pain and has better effect than the single glucosamine and the combination of the glucosamine and the pharmaceutical ingredients.

Each embodiment in the description is described in a progressive way. The difference of each embodiment from each other is the focus of explanation. The same and similar parts among all of the embodiments can be referred to each other. For a method disclosed by the embodiments, because the method corresponds to a method disclosed by the embodiments, the method is simply described. Refer to the description of the method part for the related part.

The above description of the disclosed embodiments enables those skilled in the art to realize or use the present invention. Many modifications to these embodiments will be apparent to those skilled in the art. The general principle defined herein can be realized in other embodiments without departing from the spirit or scope of the present invention. Therefore, the present invention will not be limited to these embodiments shown herein, but will conform to the widest scope consistent with the principle and novel features disclosed herein.

What is claimed is:

1. A compound composition with function of promoting bone and joint health, wherein the compound composition is composed of the following raw materials in parts by weight:

| | |
|---|---|
| glucosamine | 1.0-3.0 parts; |
| collagen | 0.1-1.0 part; |
| chondroitin sulfate | 0.1-1.0 part; and |
| traditional Chinese medicine extract | 0.1-1.0 part; | wherein
the traditional Chinese medicine extract is a mixture composed of at least two extracts of an epimedium brevicornu extract, a salviae miltiorrhizae extract, a dioscorea nipponica makino extract, a rhizoma drynariae extract and a dodder extract;
wherein the traditional Chinese medicine extract is prepared by extracting traditional Chinese medicine;
wherein the traditional Chinese medicine comprises the following components in parts by weight: 7-12 parts of epimedium brevicornu, 0.5-3 parts of salviae miltiorrhizae, 6.5-9 parts of dioscorea nipponica makino, 1-5 parts of rhizoma drynariae and 1-5 parts of dodder.

2. The compound composition with function of promoting bone and joint health according to claim 1, wherein the compound composition is composed of the following raw materials in parts by weight:

| | |
|---|---|
| glucosamine | 1.0-1.5 parts; |
| collagen | 0.2-0.7 part; |
| chondroitin sulfate | 0.1-0.3 part; and |
| traditional Chinese medicine extract | 0.1-0.5 part. |

3. The compound composition with function of promoting bone and joint health according to claim 2, wherein the compound composition is composed of the following raw materials in parts by weight:

| | |
|---|---|
| glucosamine | 1.2 parts; |
| collagen | 0.4 part; |
| chondroitin sulfate | 0.2 part; and |
| traditional Chinese medicine extract | 0.35 part. |

* * * * *